United States Patent
Webb

(10) Patent No.: US 6,629,384 B2
(45) Date of Patent: *Oct. 7, 2003

(54) METHOD FOR ELIMINATING SEED AND FRUIT DEBRIS PRODUCED BY FLOWERING PLANTS

(76) Inventor: Roger S. Webb, 11406 SW. 16th St., Micanopy, FL (US) 32667

(*) Notice: Subject to any disclaimer, the term of this patent is extended or adjusted under 35 U.S.C. 154(b) by 0 days.

This patent is subject to a terminal disclaimer.

(21) Appl. No.: 10/090,197

(22) Filed: Mar. 4, 2002

(65) Prior Publication Data

US 2002/0144459 A1 Oct. 10, 2002

Related U.S. Application Data

(63) Continuation-in-part of application No. 09/493,913, filed on Jan. 28, 2000, now Pat. No. 6,360,479.
(60) Provisional application No. 60/144,263, filed on Jul. 15, 1999.

(51) Int. Cl.$^7$ .......................... A01G 29/00; A01G 17/18
(52) U.S. Cl. .................................. 47/57.5; 47/8; 47/48.5
(58) Field of Search ............................ 47/57.5, 8, 58.1, 47/48.5

(56) References Cited

U.S. PATENT DOCUMENTS 4,144,673 A    3/1979    Quast et al.

OTHER PUBLICATIONS

Sexton, Roy and Roberts, Jeremy A.; Cell Biology of Abscission, 198 Annual Review of Plant Physiology, vol. 33, pp. 133–162.

Davies, Mauseth, Raven, Salisbury and Ross, Biosynthesis and Metabolism of Auxin, www.bio.metu.tr/~e068741/project/auxin.html, p. 3,4.

Clarke, Robert Connell, Marijuana Botany, http://users.lycaeum.org/~sunny/botany2.htm. 14 pages.

Primary Examiner—Peter M. Poon
Assistant Examiner—Andrea M. Valenti
(74) Attorney, Agent, or Firm—Hodgson Russ LLP

(57) ABSTRACT

A method of deflowering hardwood trees (dicots) comprises the steps of evaluating the physiological maturity of male and female flowers of a dicot, and injecting a solution containing synthetic indolebutyric acid (IBA) into vascular tissue of the tree when male and female flowers approach physiological maturity at or prior to fertilization. In accordance with a preferred method, the injected solution is about 4% synthetic IBA in water, and five milliliters of the solution is injected into the vascular tissue through each of a plurality of injection holes bored at spaced intervals about the circumference of the trunk of the dicot. The method causes delayed shedding of staminate flowers and early abortion or suppression of pistillate flowers, thereby preventing the development of fruit heads and the production of seed known to be a nuisance.

37 Claims, 1 Drawing Sheet

METHOD FOR ELIMINATING SEED AND FRUIT DEBRIS PRODUCED BY FLOWERING PLANTS

CROSS-REFERENCE TO RELATED APPLICATIONS

This is a continuation-in-part application claiming benefit under 35 U.S.C. §120 of U.S. patent application Ser. No. 09/493,913 filed Jan. 28, 2000, now U.S. Pat. No. 6,360,479 and claims benefit under 35 U.S.C. §119 of U.S. Provisional Patent Application No. 60/144,263 filed Jul. 15, 1999.

BACKGROUND OF THE INVENTION

The present invention relates generally to the field of arboriculture, and more particularly, to a method of eliminating unwanted seed and fruit debris from a variety of flowering trees classified as dicots.

Dicots, commonly referred to as hardwood trees, are grown throughout the world for commercial wood and fiber production and for landscape enhancement. However, subsequent to fertilization of the plant's flowers during springtime, many dicots produce considerable seed and fruit debris upon the ground in their immediate vicinity. Often, the seed and fruit debris is a nuisance that must be cleared away, particularly if it falls upon walkways or the like. Attempts to deflower such trees prior to fertilization have heretofore involved spraying individual flowers of the tree with such chemicals as FLOREL®. This procedure is time consuming, requires the use of people lifters for positioning an chemical application specialist adjacent to the tree canopy for access to the flowers, and presents environmental concerns.

SUMMARY OF THE INVENTION

It is therefore an object of the present invention to reduce the likelihood of successful fertilization in dicots by interrupting the normal process of male and female flower maturation, male pollen production, and female flower fertilization to prevent the ultimate formation of fruit heads and seed.

It is another object of the present invention to obviate the need for manually deflowering dicots by providing a method for doing so chemically.

It is another object of the present invention to provide a method for deflowering dicots that can be performed from the ground.

It is a further object of the present invention to provide a method of chemically deflowering dicots using micro- and macro-injection techniques.

The deflowering method of the present invention comprises the steps of evaluating the physiological maturity of male and female flowers of a dicot, and injecting a solution containing synthetic indolebutyric acid (IBA) into vascular tissue of the dicot when male and female flowers approach physiological maturity at or prior to fertilization. In accordance with a preferred procedure, the injected solution is about 4% synthetic IBA in water, and five milliliters of the solution is injected into the vascular tissue through each of a plurality of injection holes bored at spaced intervals about the circumference of the trunk of the dicot. The method causes delayed shedding of staminate flowers and early abortion or suppression of pistillate flowers, thereby preventing the development of fruit heads and the production of seed.

BRIEF DESCRIPTION OF THE DRAWINGS

The nature and mode of operation of the present invention will now be more fully described in the following detailed description of preferred embodiments taken with the accompanying drawing figure, in which.

DETAILED DESCRIPTION OF THE INVENTION

Figure 1:
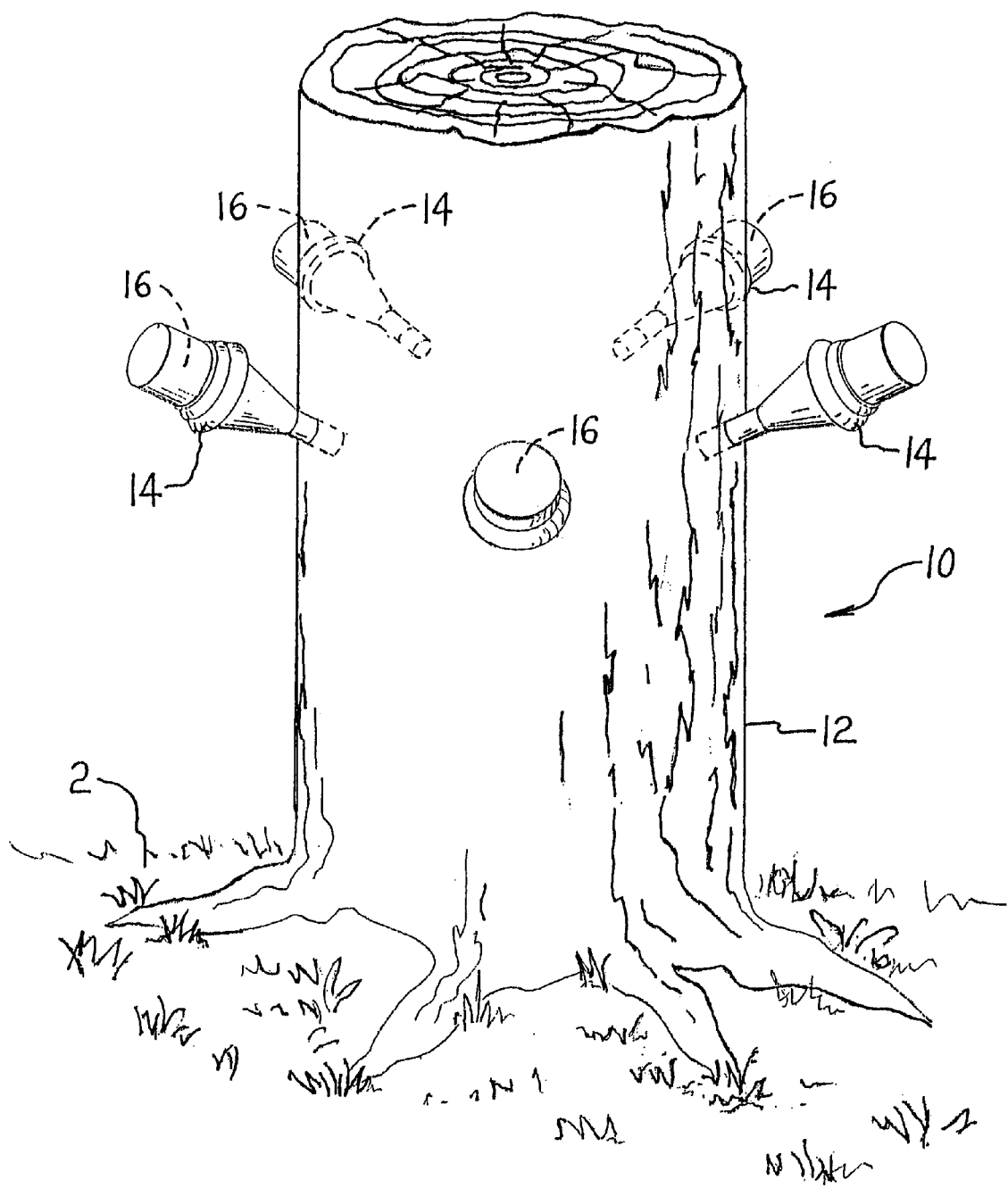
FIG. 1 is a perspective view illustrating a method of deflowering a dicot in accordance with a preferred embodiment of the present invention.

FIG. 1 illustrates generally an injection step in accordance with a method of the present invention. It will become apparent from reading the several examples set forth hereinbelow that the injection step follows an initial step of evaluating the physiological maturity of male and female flowers of the tree to be injected, as described in each specific example.

In FIG. 1, the reference numeral 10 generally indicates a tree to be deflowered, and reference numeral 12 specifically indicates the trunk of tree 10 growing out of ground 2. A plurality of injection units 14 are positioned at regular intervals about the circumference of trunk 12, with a discharge tube of each injection unit being inserted within a preformed injection hole bored or drilled at an angle through the bark of trunk 12 to communicate with vascular tissue of tree 10. Injection units 14 are preferably micro-injection units designed for use with injection holes that are less than $\frac{3}{8}$ of an inch in diameter. A suitable micro-injection unit for practicing the present invention is disclosed, for example, in U.S. Pat. No. 5,249,391. Although micro-injection units are preferred as being less stressful to the tree, macro-injection units that are designed for use with injection holes that are $\frac{3}{8}$ of an inch or greater in diameter and at least two inches in depth are also useful in carrying out injections for purposes of the present invention.

Injection units 14 each include a reservoir carrying a supply of solution 16 containing indolebutyric acid (IBA). A dilute solution of from 3% to 5% IBA in distilled water is recommended, and a dilute solution of 4% IBA in distilled water has been used in the various experimental trials described below. Injection units carrying dilute IBA solution marketed under the trademark SNIPPER™ and available from Tree Tech Microinjection Systems of Morriston, Fla. are particularly suitable for practicing the method of the present invention.

IBA has long been associated with the commercial production of ornamental or agronomic plant species by promoting the generation of new roots on succulent vegetative cuttings. With the exception of Applicant's own teaching provided in U.S. patent application Ser. No. 09/493,913 and U.S. Provisional Patent Application No. 60/144,263 on which the present application is based, Applicant is unaware of any prior art describing the injection or other application of IBA to trees for deflowering purposes. IBA is known to undergo fatty acid hydrolysis in treated cuttings whereby it is converted to indoleacetic acid (IAA), which is thought to provide the hormonal stimulus for tissue de-differentiation at the cut edge of the shoot to re-form cells into functional vascular tissue. Accordingly, the method of the present invention also encompasses injecting a solution containing IAA into the vascular system of tree 10.

EXAMPLE #1

Genus Ailanthus, Species *A. altissima*, a.k.a. "Tree-of-Heaven"

Cooperator: Lucas Tree Experts (Portland, Me.)

Five tree-of-heaven trees were selected for injection of SNIPPER™ microinjection units each containing 5 mL of 4% indole-3-butyric acid (IBA) in the suburban Portland area. An equal number of trees were selected as untreated controls. An average of six microinjection units were used for each treated tree. The purpose of this trial was to determine the efficacy of IBA injections for potential control of flower formation and subsequent fertilization in an attempt to prematurely deflower trees to prevent seed formation. The study was begun on May 2nd concluded on Jul. $21^{st}$, 2000.

Tree-of-heaven flowers were small and yellow-green. These flowers were polygamous, dioecious and occurred in panicles. Physiological maturity was judged from the appearance of a nearly fully expanded five-lobed calyx as well as upright and elongated stamens in the male flowers, although this was not particularly easy given the small size of the flowers. Approximately five-to-seven days after injection, the color of flowers on treated trees changed from a healthy yellow-green color to a brownish-yellow color indicating a moribund condition. Ten-to-fourteen days after injection, there were no flowers, either moribund or dead, left on the treated trees. Untreated trees exhibited large numbers of flowers and the young samara were observed to be developing normally.

EXAMPLE #2

Genus Prunus, Species *P. serotina*, a.k.a. "Black Cherry"

Cooperator: Danise & Associates (Charlotte, N.C.)

Six trees in the Pence Road area were injected with SNIPPER™ microinjection units each containing 5 mL of 4% indole-3-butyric acid (IBA) solution spaced at six-inch intervals around the circumference of the tree. Injected trees were selected on the basis of near maximum flower extension in the early spring indicating that these flowers were nearing physiological maturity. An equal number of trees was selected as a control group. The average number of microinjection units per tree was five. The goal was to determine if the plant growth regulator effects of IBA could be used to interrupt normal floral physiology and prevent flower fertilization and prevent any subsequent cherry fruit formation. The study was initiated on Apr. 10th and concluded on Jun. $2^{nd}$, 2000.

The floral component consisted of many-flowered, loose racemes that tended to appear simultaneously in the spring. The canopy was filled with flowers that were very close in developmental timing and thus presented a common optimal stage at which to inject trees for maximum deflowering effect. Within approximately five days after injection, cherry flowers were collapsing and appeared non-functional. After five-to-ten days more, flowers of injected trees were mostly cast from treated trees. No fruit was observed to form on treated trees, while uninjected trees experienced normal black, globose fruit development.

EXAMPLE #3

Genus Acer, Species *A. rubrum*, a.k.a. "Red Maple"

Cooperator: Florida Silvics, Inc. (Gainesville, Fla.)

Five trees near Paines Prairie Preserve were selected for microinjection trials of 5 mL of 4% IBA to evaluate the potential for disrupting floral physiology to prevent formation of the characteristic purplish-red polygamous flowers. The flower clusters of red maple are usually the first of any hardwood species in northern Florida to appear as winter is ending and thus are easy to observe for size and, accordingly, physiological maturity. The study was begun on Feb. 6th and concluded on Apr. 22, 2001.

Red maple flowers of injected trees were obviously affected and appeared moribund five-to-seven days after treatment. Within ten-to-fourteen days after treatment, virtually all flowers were either dead or appeared dying. Immediate casting of dead flowers from treated trees was delayed presumably due to the lingering cold weather but by the end of the study, no injected tree exhibited the presence of any flowers or any developing winged fruit. Untreated trees exhibited ample clusters of developing fruit that appeared to be developing normally.

EXAMPLE #4

Genus Carya, Species *C. glabra*, a.k.a. "Pignut Hickory"

Cooperator: Florida Silvics, Inc. (Micanopy, Fla.)

Five pignut hickory trees were selected for SNIPPER™ microinjection trials of 5 mL of 4% IBA per unit. An average of four microinjection units were applied to each tree. An equal number of trees were selected as untreated controls. The goal was to evaluate the potential deflowering ability of this aqueous plant hormone solution for disrupting the floral maturation process and accusing the premature deflowering of hickory trees. Timing of injection trials was based on the nearness of floral physiological maturity as noted by the full or nearly-full extension of staminate flowers, particularly each flower's three-branched aments. When these aments appeared to be first extended to a maximum length, test trees were injected. The study was begun on Feb. $10^{th}$ and concluded on Apr. 22, 2001.

These three-branched aments were easily observable and the determination of the proper timing for injection of SNIPPER™ was comparatively easy. Usually within three-to-five days after treatment, these aments appeared dehydrated and dull in color, which were symptoms associated with a moribund condition. Flowers of treated trees were discharged readily and within seven days after injection, no flowers remained on the trees. Untreated trees continued to exhibit normal flower and fruit development. No hickory nuts developed in treated trees that were in sharp contrast to untreated trees.

EXAMPLE #5

Genus Celtis, Species *C. occidentalis*, a.k.a. "Hackberry"

Cooperator: Old Tree Preservation (Tupelo, Miss.)

Eight trees were selected and injected with SNIPPER™ microinjection units each containing 5 mL of 4% indole-3-butyric acid (IBA) solution spaced at six-inch intervals around the circumference of the tree. Injected trees were selected on the basis of near maximum flower extension in the early spring indicating that these flowers were nearing physiological maturity. An equal number of trees were selected as a control group. The average number of microinjection units per tree was five. The goal was to determine if the plant growth regulator effects of IBA could be used to interrupt normal flower physiology and prevent any subsequent berry formation. The study was initiated on Apr. $20^{th}$ and concluded on Jun. 4th, 2001.

The flowers are minute and either polygamomonoecious or rarely monoecious. Staminate flowers occurred in fascicles toward the base of twigs and above these occurred the pistillate flowers. Pistillate flowers occurred either solitary or in few-flowered fascicles. Although small, hackberry flower development was relatively easy to determine and as these flowers elongated and approached maximum development, microinjection of SNIPPER™ resulted in complete eradication of flowers in treated trees. Accordingly, treated trees produced no young berries by the end of the experiment. Normal berry formation was observed among untreated trees. Approximately five days after injection, hackberry flowers appeared dehydrated and moribund. With 10 days after injection, flowers were dead and mostly cast from treated trees.

EXAMPLE #6

Genus Diospyros, Species *D. virginiana*, a.k.a. "Common Persimmon"

Cooperator: Florida Silvics, Inc. (Gainesville, Fla.)

Eight trees were selected and injected with SNIPPER™ microinjection units each containing 5 mL of 4% indole-3-butyric acid (IBA) solution spaced at six-inch intervals around the circumference of the tree. Injected trees were selected on the basis of near maximum flower extension in the early spring indicating that these flowers were nearing physiological maturity. An equal number of trees were selected as a control group. The average number of microinjection units per tree was five. The goal was to determine if the plant growth regulator effects of IBA could be used to interrupt normal flower physiology and prevent any subsequent berry formation. The study was initiated on Apr. $20^{th}$ and concluded on Jun. 4th, 2001.

Persimmon flowers are regular and dioecious and are 0.5-to-0.75 inch long. These are yellow-green and appear in conjunction with early foliage expansion. If allowed to fertilize, individual globose, orange-to-purple berries approximately 1-to-1.5 inches long would be produced which are considered nuisance fruit. Microinjection of treated trees was begun on Feb. $18^{th}$ when early flowers were observed to be present. After approximately three-to-five days, flowers appeared dehydrated and moribund. Seven-to-ten days after injection, flowers appeared dead and many were cast from the trees. No berry formation was observed among treated trees while berry formation proceeded normally among untreated trees. The study was concluded on Apr. $10^{th}$, 2001.

EXAMPLE #7

Genus Fraxinus, Species *F. pennsylvanica*, a.k.a. "Green Ash"

Cooperator: Florida Silvics, Inc. (Gainesville, Fla.)

Six trees were selected near the University of Florida campus in Gainesville and injected with SNIPPER™ microinjection units each containing 5 mL of 4% indole-3-butyric acid (IBA) solution spaced at six-inch intervals around the circumference of the tree. Injected trees were selected on the basis of near maximum flower extension in the early spring indicating that these flowers were nearing physiological maturity. An equal number of trees were selected as a control group. The average number of microinjection units per tree was four. The goal was to determine if the plant growth regulator effects of IBA could be used to interrupt normal flower physiology and prevent any subsequent berry formation. The study was initiated on Feb. 23rd and concluded on Apr. 16, 2001.

Flowers were dioecious and occurred in compact panicles. Flowers occurred in conjunction with appearance of early foliage. Within five days, flowers from treated trees appeared dehydrated and moribund. Within fourteen days after injection, flowers from treated trees were dead and cast from the trees. Flowers on untreated trees appeared to fertilize normally and the typically narrow lanceolate fruit were easily observed forming by the end of the study. No fruit was observed on treated trees by the end of the study.

EXAMPLE #8

Genus Gingko, Species *G. biloba*, a.k.a. "Common Gingko" or "Maidenhair Tree"

Cooperator: Bartlett Tree Expert Company (Philadelphia, Penn.)

Ten trees were selected near a downtown commercial district in Philadelphia and injected with SNIPPER™ microinjection units each containing 5 mL of 4% indole-3-butyric acid (IBA) solution spaced at six-inch intervals around the circumference of the tree. Injected trees were selected on the basis of near maximum flower extension in the early spring indicating that these flowers were nearing physiological maturity. An equal number of trees were selected as a control group. The average number of microinjection units per tree was five. The goal was to determine if the plant growth regulator effects of IBA could be used to interrupt normal flower physiology and prevent any subsequent berry formation. The study was initiated on May 2nd and concluded on Jul. 20th, 2001.

Male flowers occurred as staminate flowering branchlets in conjunction with the appearance of young foliage. Within seven days, flowers from treated trees appeared dehydrated and moribund. Within fourteen days after injection, flowers from treated trees were dead and mostly cast from the trees. Flowers on untreated trees appeared to fertilize normally and the typically globose, individual fruit were easily observed forming by the end of the study. Fruit when mature appear yellow and are considered nuisance fruit since when cast from trees the fruit emit an odor similar to rancid butter during decomposition. No fruit was observed on treated trees by the end of the study.

EXAMPLE #9

Genus Gleditsia, Species *G. triacanthos*, a.k.a. "Honey Locust"

Cooperator: Danise & Associates (Charlotte, N.C.)

Five trees were selected near a downtown restored residential district in Charlotte and injected with SNIPPER™ microinjection units each containing 5 mL of 4% indole-3-butyric acid (IBA) solution spaced at six-inch intervals around the circumference of the tree. Injected trees were selected on the basis of near maximum flower extension in the early spring indicating that these flowers were nearing physiological maturity. An equal number of trees were selected as a control group. The average number of microinjection units per tree was six. The goal was to determine if the plant growth regulator effects of IBA could be used to interrupt normal flower physiology and prevent any subsequent berry formation. The study was initiated on Apr. 5th and concluded on Jun. 10th, 2001.

Flowers occurred as small polygamous axillary racemes that appeared after the initiation of young foliage. Within five-to-seven days, flowers from treated trees appeared dehydrated and moribund. Within ten-to-twelve days after injection, flowers from treated trees were dead and mostly cast from the trees. Flowers on untreated trees appeared to fertilize normally and the typically twisted, leguminous fruit were easily observed forming by the end of the study. Fruit when mature appeared as brown seedpods and were considered nuisance fruit due to the difficulty of landscape clean up after being cast from trees. No fruit was observed on treated trees by the end of the study.

EXAMPLE #10

Genus Juglans, Species *J. nigra*, a.k.a. "Black Walnut"

Cooperator: Florida Silvics, Inc. (Gainesville, Fla.)

Five trees were selected in a plot north of Interstate-75 near Madison and injected with SNIPPER™ microinjection units each containing 5 mL of 4% indole-3-butyric acid (IBA) solution spaced at six-inch intervals around the circumference of the tree. Injected trees were selected on the basis of near maximum flower extension in the early spring indicating that these flowers were nearing physiological maturity. An equal number of trees were selected as a control group. The average number of microinjection units per tree was six. The goal was to determine if the plant growth regulator effects of IBA could be used to interrupt normal flower physiology and prevent any subsequent berry formation. The study was initiated on Mar. 12th and concluded on May 16th, 2001.

Flowers were monoecious, apetalous and occurred as staminate flowering branchlets in conjunction with the appearance of young foliage. Staminate flowers occurred in pre-formed unbranched aments and pistillate flowers occurred in spikes of two-to-eight flowers. Within five-to-seven days, flowers from treated trees appeared dehydrated and moribund. Within twelve-to-fourteen days after injection, flowers from treated trees were dead and mostly cast from the trees. Flowers on untreated trees appeared to fertilize normally and the typical fruit, i.e., individual drupe-like nuts encased in a yellowish semi-fleshy, indehiscent husk were easily observed forming by the end of the study. Fruit when mature are considered a nuisance since when cast from trees the fruit are large (approximately two inches in diameter) and unwieldy to collect in the landscape. No fruit was observed on treated trees by the end of the study.

EXAMPLE #11

Genus Malus, Example Malus cvs., a.k.a. "Flowering Crabapple" Cultivars)

Cooperator, Warne Chemical and Equipment Co. (Rapid City, S.Dak.)

Five trees were selected in selected ornamental landscapes around Rapid City and injected with SNIPPER™ microinjection units each containing 5 mL of 4% indole-3-butyric acid (IBA) solution spaced at six-inch intervals around the circumference of the tree. Injected trees were selected on the basis of near maximum flower extension in the early spring indicating that these flowers were nearing physiological maturity. An equal number of trees were selected as a control group. The average number of microinjection units per tree was three. The goal was to determine if the plant growth regulator effects of IBA could be used to interrupt normal flower physiology and prevent any subsequent berry formation. The study was initiated on May 10th and concluded on Jul. 15th, 2001.

Flowers were dioecious, fragrant and occurred after the appearance of young foliage. Clusters of flowers were considered physiologically mature after first reaching a maximum size of about 0.5 inches across. Within seven-to-ten days, flowers from treated trees appeared dehydrated and moribund. Within fourteen-to-eighteen days after injection, flowers from treated trees were dead and mostly cast from the trees. Flowers on untreated trees appeared to fertilize normally and the typical crabapple fruit were easily observed forming in abundance by the end of the study. Crabapple fruit when mature are considered a nuisance since when cast from trees in late autumn the fruit are large, numerous and time-consuming to collect in the landscape. Some fruit were observed on treated trees at the end of the study and their presence was assumed due to late injection, i.e., some of the flowers in the numerous flower clusters successfully fertilized before injection was conducted.

EXAMPLE #12

Genus Olea, Species *O. europaea*, a.k.a. "Ornamental Olive"

Cooperator: Bartlett Tree Expert Co. (Sacramento, Calif.)

Eight trees were selected in selected urban street landscapes in Sacramento and injected with SNIPPER™ microinjection units each containing 5 mL of 4% indole-3-butyric acid (IBA) solution spaced at six-inch intervals around the circumference of the tree. Injected trees were selected on the basis of near maximum flower extension in the early spring indicating that these flowers were nearing physiological maturity. An equal number of trees were selected as a control group. The average number of microinjection units per tree was two. The goal was to determine if the plant growth regulator effects of IBA could be used to interrupt normal flower physiology and prevent any subsequent berry formation. The study was initiated on Apr. 17th and concluded on Jul. 1st, 2001.

Flowers were dioecious, fragrant and were largely hidden by evergreen leaves that made determination of physiological maturity more difficult than other plant genera tested. Clusters of flowers were considered physiologically mature after first reaching maximum size. Within five-to-seven days, flowers from treated trees appeared dehydrated and moribund. Within ten-to-twelve days after injection, flowers from treated trees were dead and mostly cast from the trees. Flowers on untreated trees appeared to fertilize normally and the typical fruit, i.e. green drupes were easily observed forming in abundance by the end of the study. Olive fruit when mature are considered a nuisance since when cast from trees when ripe their oval shape permits them to roll some distance from trees. When planted in ornamental or urban landscapes, olives pose a safety problem by interfering with pedestrian traffic and creating dangerous road conditions when they collect on road surfaces. Some olive fruit were observed on treated trees at the end of the study and their presence was assumed due to injections occurring some flowers successfully fertilized.

EXAMPLE #13

Genus Platanus, Species *P. occidentalis*, a.k.a. "American Sycamore"

Cooperator, Florida Silvics, Inc. (Gainesville, Fla.)

Five trees were selected in selected urban landscapes in Gainesville and injected with SNIPPER™ microinjection units each containing 5 mL of 4% indole-3-butyric acid (IBA) solution spaced at six-inch intervals around the circumference of the tree. Injected trees were selected on the basis of near maximum flower extension in the early spring indicating that these flowers were nearing physiological maturity. An equal number of trees were selected as a control group. The average number of microinjection units per tree was six. The goal was to determine if the plant growth regulator effects of IBA could be used to interrupt normal flower physiology and prevent any subsequent berry formation. The study was initiated on Mar. 2nd and concluded on Jun. 6th, 2001.

Flowers were monecious with male and female flowers occurring in different heads comprised of several of the minute individual flowers. Flowers appeared with the emerging young foliage. Clusters of flower heads were considered physiologically mature after first reaching a maximum size of approximately 0.5 inch tall. Within five-to-seven days, flowers from treated trees appeared dehydrated and moribund. Within ten-to-twelve days after injection, flowers from treated trees were dead and mostly cast from the trees. Flowers on untreated trees appeared to fertilize normally and the typical fruit, i.e. multiple, globose fruit about 1.25 inches in maximum diameter when mature were easily observed forming in abundance by the end of the study. Sycamore fruit when mature are considered a nuisance since these from in abundant numbers and when cast from trees created a widespread clean-up problem. When planted in ornamental or urban landscapes, sycamore fruit pose a safety problem by interfering with pedestrian traffic when they collect on sidewalk and driveway surfaces.

EXAMPLE #14

Genus Populus, Species *P. angustifolia*, a.k.a. "Narrowleaf Cottonwood")

Cooperator: Warne Chemical & Equipment Co. (Rapid City, S.Dak.)

Six trees were selected in ornamental landscapes near Rapid City and injected with SNIPPER™ microinjection units each containing 5 mL of 4% indole-3-butyric acid (IBA) solution spaced at six-inch intervals around the circumference of the tree. Injected trees were selected on the basis of near maximum flower extension in the early spring indicating that these flowers were nearing physiological maturity. An equal number of trees were selected as a control group. The average number of microinjection units per tree was six. The goal was to determine if the plant growth regulator effects of IBA could be used to interrupt normal flower physiology and prevent any subsequent berry formation. The study was initiated on May $5^{th}$ and concluded on Jul. 16th, 2001.

Flowers were dioecious with male and female flowers both occurring in druping aments appearing from separate buds before appearance of young foliage. Clusters of flower heads were considered physiologically mature after first reaching maximum size of approximately 0.25 inch. Within five-to-seven days, flowers from treated trees appeared dehydrated and moribund. Within ten-to-twelve days after injection, flowers from treated trees were dead and mostly cast from the trees. Flowers on untreated trees appeared to fertilize normally and the typical fruit, i.e. subglobose capsule containing small seed tufted with long silky hairs, were readily observed forming in abundance by the end of the study. Cottonwood fruit when mature are considered a nuisance since the long silky hairs associated with seeds provide excellent buoyancy and seeds travel by wind long distances from parent trees. Viability is low and germination must occur within a few days after discharge but large numbers of seeds create a serious clean-up problem in ornamental landscapes.

EXAMPLE #15

Genus Quercus, Species *Q. nigra*, a.k.a. "Water Oak"

Cooperator: Florida Silvics, Inc. (Gainesville, Fla.)

Five trees were selected in two ornamental landscapes near Micanopy and injected with SNIPPER™ microinjection units each containing 5 mL of 4% indole-3-butyric acid (IBA) solution spaced at six-inch intervals around the circumference of the tree. Injected trees were selected on the basis of near maximum staminate flower extension in the early spring indicating that these flowers were nearing physiological maturity. An equal number of trees were selected as a control group. The average number of microinjection units per tree was eight. The goal was to determine if the plant growth regulator effects of IBA could be used to interrupt normal flower physiology and prevent any subsequent berry formation. The study was initiated on Feb. 23rd and concluded on Apr. 21st, 2001.

Flowers were dioecious with staminate flowers occurring in clustered aments appearing before the production of young foliage. Pistillate flowers were present in spikes but staminate flowers were much more obvious. Staminate flowers were used as the marker for injection occurrence and were considered physiologically mature after aments reached a maximum size of approximately 2.0 inches. Within three-to-five days, flowers from treated trees appeared dehydrated and moribund. Within seven-to-ten days after injection, flowers from treated trees were dead and mostly cast from the trees. Flowers on untreated trees appeared to fertilize normally and the acorn fruit were readily observed forming in abundance by the end of the study. Acorns when mature are considered a nuisance since these are difficult to remove from lawns and other landscaping areas and pose a safety hazard to pedestrians when they are produced in large numbers.

EXAMPLE #16

Genus Robinia, Species *R. pseudoacacia*, a.k.a. "Black Locust"

Cooperator, Danise & Associates (Charlotte, N.C.)

Eight trees were selected in three ornamental landscapes in Charlotte and injected with SNIPPER™ microinjection units each containing 5 mL of 4% indole-3-butyric acid (IBA) solution spaced at six-inch intervals around the circumference of the tree. Injected trees were selected on the basis of near maximum staminate flower extension in the early spring indicating that these flowers were nearing physiological maturity. An equal number of trees were selected as a control group. The average number of microinjection units per tree was four. The goal was to determine if the plant growth regulator effects of IBA could be used to interrupt normal flower physiology and prevent any subsequent berry formation. The study was initiated on Apr. 13th and concluded on Jun. 15th, 2001.

Flowers were perfect, papilionaceous and fragrant occurring in racemes. Flowers occurred after the production of young foliage. Flowers were determined to be near physiological maturity after reaching a maximum size of approximately 1.5 inches. Within five-to-seven days, flowers from treated trees appeared dehydrated and moribund. Within ten-to-fourteen days after injection, flowers from treated trees were dead and mostly cast from the trees. Flowers on untreated trees appeared to fertilize normally and the typical linear-oblong legume fruit were readily observed forming in abundance by the end of the study. These legume pods when mature are considered a nuisance since these are difficult to collect from lawns and other landscaping areas and decompose slowly.

What is claimed is:

1. A method of deflowering a dicot comprising the steps of:

(A) evaluating the physiological maturity of male and female flowers of said dicot; and (B) injecting a solution containing synthetic indolebutyric acid into vascular tissue of said dicot, said step of injecting said solution being performed when male and female flowers of said dicot approach physiological maturity at or prior to fertilization.

2. The method according to claim 1, wherein said solution is about 4% synthetic indolebutyric acid in water.

3. The method according to claim 1, wherein said solution is injected into said vascular tissue through a plurality of injection holes bored at spaced intervals about the circumference of the trunk of said dicot.

4. The method according to claim 3, wherein said plurality of injection holes are spaced approximately six inches apart about said circumference.

5. The method according to claim 4, wherein said solution is about 4% synthetic indolebutyric acid in water, and about five milliliters of said solution is injected through each of said plurality of injection holes.

6. The method according to claim 1, wherein said dicot is of the genus Ailanthus.

7. The method according to claim 6, wherein said dicot is of the species *A. altissima*.

8. The method according to claim 1, wherein said dicot is of the genus Prunus.

9. The method according to claim 8, wherein said dicot is of the species *P. serotina*.

10. The method according to claim 1, wherein said dicot is of the genus Acer.

11. The method according to claim 10, wherein said dicot is of the species *A. rubrum*.

12. The method according to claim 1, wherein said dicot is of the genus Carya.

13. The method according to claim 12, wherein said dicot is of the species *C. glabra*.

14. The method according to claim 1, wherein said dicot is of the genus Celtis.

15. The method according to claim 14, wherein said dicot is of the species *C. occidentalis*.

16. The method according to claim 1, wherein said dicot is of the genus Diospyros.

17. The method according to claim 16, wherein said dicot is of the species *D. virginiana*.

18. The method according to claim 1, wherein said dicot is of the genus Fraxinus.

19. The method according to claim 18, wherein said dicot is of the sp des *F. pennsylvanica*.

20. The method according to claim 1, wherein said dicot is of the genus Gingko.

21. The method according to claim 20, wherein said dicot is of the species *G. biloba*.

22. The method according to claim 1, wherein said dicot is of the genus Gleditsia.

23. The method according to claim 22, wherein said dicot is of the species *G. triacanthos*.

24. The method according to claim 1, wherein said dicot is of the genus Juglans.

25. The method according to claim 24, wherein said dicot is of the species *J. nigra*.

26. The method according to claim 1, wherein said dicot is of the genus Malus.

27. The method according to claim 26, wherein said dicot is a flowering crabapple cultivar.

28. The method according to claim 1, wherein said dicot is of the genus Olea.

29. The method according to claim 28, wherein said dicot is of the species *O. europaea*.

30. The method according to claim 1, wherein said dicot is of the genus Platanus.

31. The method according to claim 30, wherein said dicot is of the species *P. occidentalis*.

32. The method according to claim 1, wherein said dicot is of the genus Populus.

33. The method according to claim 32, wherein said dicot is of the species *P. angustifolia*.

34. The method according to claim 1, wherein said dicot is of the genus Quercus.

35. The method according to claim 34, wherein said dicot is of the species *Q. nigra*.

36. The method according to claim 1, wherein said dicot is of the genus Robinia.

37. The method according to claim 36, wherein said dicot is of the species *R. pseudoacacia*.

* * * * *